(12) United States Patent
Liu

(10) Patent No.: US 10,905,886 B2
(45) Date of Patent: Feb. 2, 2021

(54) IMPLANTABLE MEDICAL DEVICE FOR DEPLOYMENT ACROSS THE ATRIOVENTRICULAR SEPTUM

(71) Applicant: CARDIAC PACEMAKERS, INC., St. Paul, MN (US)

(72) Inventor: Lili Liu, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 1040 days.

(21) Appl. No.: 15/392,668

(22) Filed: Dec. 28, 2016

(65) Prior Publication Data
US 2017/0182327 A1 Jun. 29, 2017

Related U.S. Application Data

(60) Provisional application No. 62/271,647, filed on Dec. 28, 2015.

(51) Int. Cl.
*A61N 1/375* (2006.01)
*A61N 1/368* (2006.01)
(Continued)

(52) U.S. Cl.
CPC .......... *A61N 1/3684* (2013.01); *A61B 5/0422* (2013.01); *A61B 5/686* (2013.01);
(Continued)

(58) Field of Classification Search
CPC ... A61B 5/6869; A61B 5/6882; A61B 5/6846; A61B 5/686; A61B 5/6865;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Eun Hwa Kim
(74) *Attorney, Agent, or Firm* — Seager, Tufte & Wickhem LLP.

(57) ABSTRACT

An implantable medical device (IMD) may be configured for deployment at a patient's atrioventricular septum in order to sense and/or pace a patient's heart. The atrioventricular septum of the patient's heart may have an atrial facing side defining part of the right atrium of the patient's heart and a ventricle facing side defining part of the left ventricle of the patient's heart. The IMD may include a first component configured to be positioned at least in part in the right atrium of the patient's heart proximate the atrioventricular septum, and a second component configured to be positioned at least in part in the left ventricle.

18 Claims, 15 Drawing Sheets

(51) Int. Cl.
   *A61B 5/042* (2006.01)
   *A61B 5/00* (2006.01)
   *A61N 1/05* (2006.01)
   *A61N 1/365* (2006.01)
   *A61N 1/372* (2006.01)

(52) U.S. Cl.
   CPC ............ *A61B 5/6869* (2013.01); *A61N 1/057* (2013.01); *A61N 1/36514* (2013.01); *A61N 1/3756* (2013.01); *A61N 1/37205* (2013.01); *A61B 5/0031* (2013.01); *A61B 5/6882* (2013.01); *A61B 2560/066* (2013.01); *A61N 1/37512* (2017.08); *A61N 1/37518* (2017.08)

(58) Field of Classification Search
   CPC ................ A61B 5/0031; A61B 5/0422; A61B 2560/066; A61N 1/3719; A61N 1/3756; A61N 1/0031; A61N 1/056; A61N 1/0563; A61N 1/0565; A61N 1/057; A61N 1/0573; A61N 1/0585; A61N 1/059; A61N 1/37205; A61N 1/37518
   See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |

(56) References Cited

U.S. PATENT DOCUMENTS

| | | |
|---|---|---|
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |

(56) References Cited

U.S. PATENT DOCUMENTS

| | | |
|---|---|---|
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,448,999 B1 * | 11/2008 | Karicherla ......... A61B 5/02158 600/486 |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |

(56) References Cited

U.S. PATENT DOCUMENTS

| | | |
|---|---|---|
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |

(56) References Cited

U.S. PATENT DOCUMENTS

| | | |
|---|---|---|
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |

(56) References Cited

U.S. PATENT DOCUMENTS

| | | |
|---|---|---|
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1* | 3/2010 | Peacock, III .......... A61N 1/057 607/9 |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |

(56) References Cited

U.S. PATENT DOCUMENTS

| | | |
|---|---|---|
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Mates |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1* | 5/2013 | Bornzin ............... A61N 1/3684 607/9 |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |

(56) References Cited

U.S. PATENT DOCUMENTS

| | | |
|---|---|---|
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Asirvatham et al., "Intramyocardial Pacing and Sensing for the Enhancement of Cardiac Stimulation and Sensing Specificity," PACE, vol. 30, pp. 748-754, Jun. 2007.

Henz et al., "Synchronous Ventricular Pacing without Crossing the Tricuspid Valve or Entering the Coronary Sinus-Preliminary Results," Journal of Cardiovascular Electrophysiology, vol. 20(12):1391-1397, Dec. 2009. doi: 10.1111/j.0540-8167.2009.01556.x.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Notification of Transmittal of the International Search Report and the Written Opinion of the International Searching Authority, or the Declaration, Jan. 29, 2016, 15 pages.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(384): 324-331, 1970.

Wegmüller, "Intra-Body Communication for Biomedical Sensor Networks," Diss. ETH, No. 17323, 1-173, 2007.

\* cited by examiner

IMPLANTABLE MEDICAL DEVICE FOR DEPLOYMENT ACROSS THE ATRIOVENTRICULAR SEPTUM

CROSS REFERENCE TO RELATED APPLICATIONS

This application claims the benefit of U.S. Provisional Patent Application Ser. No. 62/271,647 filed on Dec. 28, 2015, the disclosure of which is incorporated herein by reference.

TECHNICAL FIELD

The present disclosure generally relates to implantable medical devices, and more particularly, to implantable medical devices that are configured to be deployed across the atrioventricular septum.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation to the heart to help the heart operate in a more normal, efficient and/or safe manner. In some instances, it may be beneficial to sense and/or pace two or more chambers of the heart.

SUMMARY

This disclosure provides design, delivery and deployment method, and clinical usage alternatives for medical devices. An example implantable medical device (IMD) configured for deployment at a patient's atrioventricular septum in order to sense and/or pace a patient's heart is disclosed, the atrioventricular septum of the patient's heart having an atrial facing side defining part of the right atrium of the patient's heart and a ventricle facing side defining part of the left ventricle of the patient's heart. The IMD includes a first component that is configured to be positioned at least in part in the right atrium of the patient's heart proximate the atrioventricular septum once the IMD is implanted and that includes a housing, a power source disposed within the housing and circuitry disposed within the housing and operably coupled to the power source. The IMD includes a second component that is configured to be positioned at least in part in the left ventricle of the patient's heart once the IMD is implanted and that is mechanically coupled to the first component through a passage passing through the atrioventricular septum. The second component includes a housing and two or more electrodes for sensing and/or pacing the left ventricle of the patient's heart.

Alternatively or additionally to any of the embodiments above, the first component further includes two or more electrodes for sensing and/or pacing the right atrium of the patient's heart.

Alternatively or additionally to any of the embodiments above, the two or more electrodes of the second component are operably coupled to the circuitry of the first component.

Alternatively or additionally to any of the embodiments above, at least one of the two or more electrodes of the second component engage the ventricle facing side of the atrioventricular septum of the patient's heart once the IMD is implanted.

Alternatively or additionally to any of the embodiments above, at least one of the two or more electrodes of the first component engage the atrial facing side of the atrioventricular septum of the patient's heart once the IMD is implanted.

Alternatively or additionally to any of the embodiments above, the second component is configured to move from a contracted state to an expanded state, wherein during implantation of the IMD, the second component is configured to pass through the passage through the atrioventricular septum in the contracted state and then move to the expanded state once in the left ventricle of the patient's heart.

Alternatively or additionally to any of the embodiments above, wherein in the expanded state, the second component extends laterally beyond a lateral extent of the passage through the atrioventricular septum and engages the ventricle facing side of the atrioventricular septum of the patient's heart.

Alternatively or additionally to any of the embodiments above, the first component extends distally beyond a delivery catheter and engages the atrial facing side of the atrioventricular septum of the patient's heart once the IMD is implanted.

Alternatively or additionally to any of the embodiments above, the second component is configured to cut the passage through the atrioventricular septum while the IMD is implanted.

Alternatively or additionally to any of the embodiments above, the second component is mechanically coupled to the first component through the passage via a connecting member.

Alternatively or additionally to any of the embodiments above, the connecting member is part of the second component, and forms an interference fit with the first component.

Alternatively or additionally to any of the embodiments above, the connecting member is part of the first component, and forms an interference fit with the first component.

Alternatively or additionally to any of the embodiments above, the first component comprises a fixation element for securing the first component to the atrioventricular septum of the patient's heart.

Alternatively or additionally to any of the embodiments above, the second component comprises a fixation element for securing the second component to the atrioventricular septum of the patient's heart.

An implantable medical device (IMD) configured for deployment at a patient's atrioventricular septum is disclosed, the atrioventricular septum of the patient's heart having an atrial facing side defining part of the right atrium of the patient's heart and a ventricle facing side defining part of the left ventricle of the patient's heart. The IMD includes a body having a first end portion, a second end portion and a connecting portion connecting the first end portion to the second end portion. At least part of the first end portion may be configured to be positioned in the right atrium of the patient's heart proximate the atrioventricular septum once the IMD is implanted and at least part of the second end portion extends into the left ventricle of the patient's heart once the IMD is implanted. The connecting portion extends through a passage that passes through the atrioventricular septum and the second end portion extends laterally beyond a lateral extent of the connecting portion to engage the ventricle facing side of the atrioventricular septum of the patient's heart once the IMD is implanted.

Alternatively or additionally to any of the embodiments above, the second end portion includes two or more electrodes for sensing and/or pacing the left ventricle of the patient's heart, wherein at least one of the two or more electrodes of the second end portion engages the ventricle facing side of the atrioventricular septum of the patient's heart.

Alternatively or additionally to any of the embodiments above, the first end portion includes two or more electrodes for sensing and/or pacing the right atrium of the patient's heart, wherein at least one of the two or more electrodes of the first end portion engages the atrial facing side of the atrioventricular septum of the patient's heart.

Alternatively or additionally to any of the embodiments above, at least part of the second end portion is configured to move from a contracted state to an expanded state.

A method of deploying a leadless pacing and sensing assembly proximate a patient's atrioventricular septum is disclosed, the leadless pacing and sensing assembly including a right atrial leadless cardiac pacemaker (LCP) and a left ventricular leadless cardiac pacemaker (LCP). The method includes advancing a delivery catheter through the patient's vasculature until a distal end of the delivery catheter is proximate an atrial side of the atrioventricular septum, the right atrial LCP disposed within a distal region of the delivery catheter. A deployment device is advanced past the right atrial LCP and through the atrioventricular septum, the left ventricular LCP secured to the deployment device such that the left ventricular LCP passes past the right atrial LCP and is disposed proximate a ventricular side of the atrioventricular septum. The left ventricular LCP is secured to the right atrial LCP and the deployment device is withdrawn.

Alternatively or additionally to any of the embodiments above, the method further comprises withdrawing the delivery catheter.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
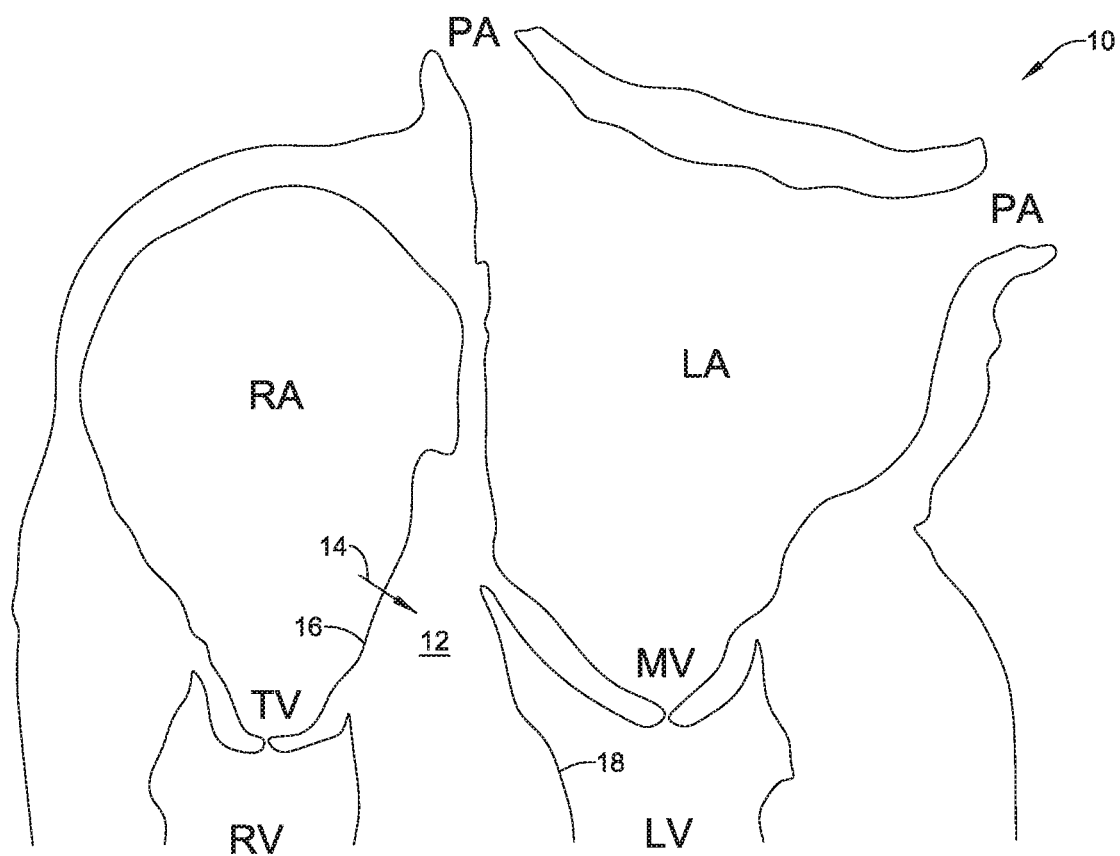
FIG. 1 is a schematic view of an upper portion of a human heart, showing the atrioventricular septum.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

The present disclosure generally relates to implantable medical devices, and more particularly, to implantable medical devices that are configured to be deployed across the atrioventricular septum. More particularly, the present disclosure is directed at providing pacing and/or sensing from a position next to or within the atrioventricular septum. In order to call out particular features of the cardiac anatomy, FIG. 1 provides a general illustration of a typical human heart 10. The heart 10 includes a right atrium RA and a left atrium LA. The left atrium LA is fluidly coupled to the pulmonary artery PA. A tricuspid valve TV separates the right atrium RA from a right ventricle RV. A mitral valve MV separates the left atrium LA from a left ventricle LV. Because the tricuspid valve TV is disposed apical (closer to the apex) of the mitral valve MV, an atrioventricular (AV) septum 12 exists. An arrow 14 indicates a portion of the AV septum 12 that may be used to provide access to both the right atrium RA and the left ventricle LV. The AV septum 12 includes an atrial side 16 that faces the right atrium RA as well as a ventricle side 18 that faces the left ventricle LV.

It will be appreciated that by traversing the AV septum 12 at or near the position indicated by the arrow 14, which is above the tricuspid valve TV and below the mitral valve MV, the left ventricle LV is accessible from the right atrium RA. This area can be reached, for example, via a transvenous catheter passing through either the SVC (superior vena cava) or the IVC (inferior vena cava) and into the right atrium RA. It will be appreciated that by deploying a two-part or multi-part LCP within the AV septum 12, it is possible to reach the left ventricle LV without having to potentially interfere with the mitral valve MV.

Figure 2:
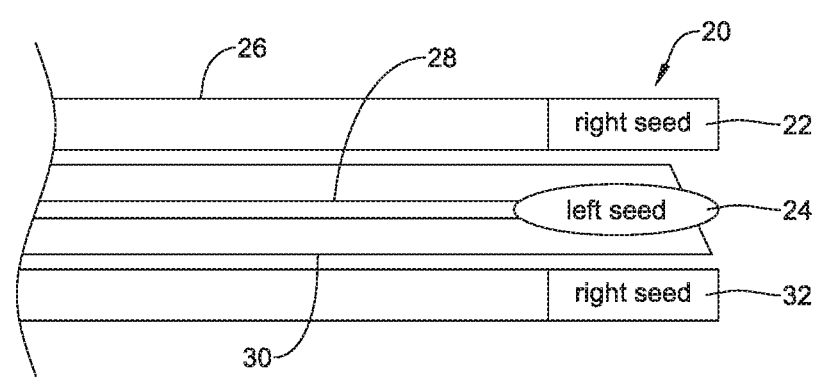
FIG. 2 is a schematic view of a dual chamber leadless cardiac pacemaker (LCP) arrangement shown in a delivery vehicle.

FIG. 2 provides a schematic view of an illustrative LCP assembly 20 that includes, as labeled, a right seed 22 and a left seed 24. In some cases, as illustrated, the right seed 22 may be configured to remain at least partially in the right atrium RA, and the left seed 24 may be configured to extend at least partially into the left ventricle LV. In some cases, the left seed 24 may be configured to pass through the right seed 22 during deployment, but this is not required. In some cases, the left seed 24 may have a diameter that is 3 French (F) or less. The illustrative LCP assembly 20 is shown disposed within a delivery catheter 26 which, as noted, may reach the right atrium RA via the SVC or the IVC. Which route is preferred may be a matter of the cardiologist's preferences, or may be at least in part a function of anatomical idiosyncrasies of a particular patient.

In some cases, the left seed 24 may be secured to a deployment mechanism 28 that can be used to advance the left seed 24 axially. The left seed 24 and the deployment mechanism 28 may be deployed within a hypotube 30 that may be configured to extend through the atrioventricular septum 12 (FIG. 1). In some cases, the hypotube 30 may have a distal end 32 that is configured to form a passage through the AV septum 12. In some instances, the distal end 32 of the hypotube 30 may be configured to poke a hole through the AV septum 12 without removing tissue from the AV septum 12. As a result, the left seed 24 may be advanced through the AV septum 12, through the hole made by the distal end 32 of the hypotube 30.

Once deployed, the left seed 24 may be disposed at least partially on the ventricular side 18 of the AV septum 12, and the right seed 22 may be disposed at least partially on the atrial side 16 of the AV septum 12 (FIG. 1). In some cases, the left seed 24 may be mechanically coupled to the right seed 22 in order to help secure the left seed 24 and the right seed 22 in place on either side of the AV septum 12. In some cases, the left seed 24 and/or the right seed 22 may include an anticoagulant coating. While not illustrated, it will be appreciated that the left seed 24 may include two or more electrodes for pacing and/or sensing within the left ventricle LV. In some cases, the electrodes on the left seed 24 may be electrically coupled with control circuitry within the right seed 22. In some cases, there may be a wired connection between the right seed 22 and the left seed 24. In some instances, there may be a wireless connection between the right seed 22 and the left seed 24.

Figure 3:
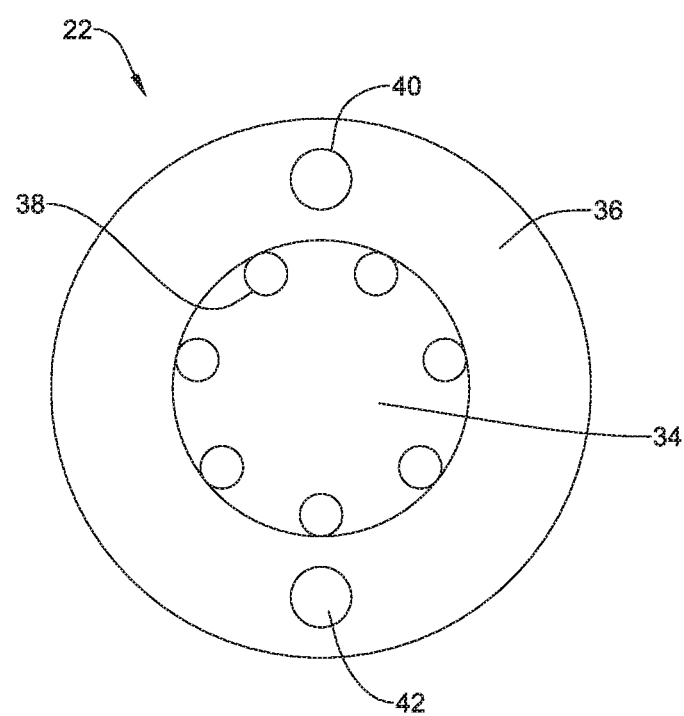
FIG. 3 is a schematic end view of the right seed of the dual chamber LCP arrangement of FIG. 2.

FIG. 3 is a schematic end view of the right seed 22 of the dual chamber LCP arrangement of FIG. 2. The illustrative right seed 22 includes a central lumen 34 extending through a body portion 36. While generically illustrated, it will be appreciated that the body portion 36 may include internal components which, for simplicity, are not illustrated here. These internal components, which will be described with respect to subsequent drawings, may include one or more of circuitry and a power supply. The central lumen 34 may be sized to accommodate the left seed 24 extended therethrough. In some cases, as illustrated, the central lumen 34 may include one or more electrodes 38 lining at least a portion of the central lumen 34 for making electrical contact with one or more corresponding electrodes (not shown) on an outer surface of the left seed 24.

In some cases, the central lumen 34 may also include one or more fixation elements (not explicitly shown) that are configured to engage with the left seed 24 and secure the left seed 24 to the right seed 22 once the left seed 24 has been deployed. The one or more fixation elements may, for example, extend to form a frictional engagement with the left seed 24. In some cases, the one or more fixation elements may be stent-like, and may expand to engage the left seed 24. In some instances, the one or more fixation elements may be formed of a shape memory material that can have a delivery shape that permits the left seed 24 to pass through the central lumen 34 of the right seed 22 and then revert to a "remembered" shape that engages the left seed 24 once the one or more fixation elements reach a particular temperature, for example. The one or more fixation elements could be formed from any of a variety of shape memory polymers or metals. In some cases, the one or more fixation elements may be formed of a nickel-titanium alloy such as Nitinol.

The right seed 22 includes, as illustrated, a first electrode 40 and a second electrode 42 that may be electrically coupled to internal circuitry within the right seed 22. While two electrodes 40, 42 are illustrated, it will be appreciated that the right seed 22 may include additional electrodes, depending on the desired pacing and/or sensing capabilities. In some cases, the first electrode 40 and the second electrode 42 may be disposed on the distal side of the right seed 22 such that both the first electrode 40 and the second electrode 42 may be in contact with the atrial side 16 of the AV septum 12 once implanted.

Figure 4:
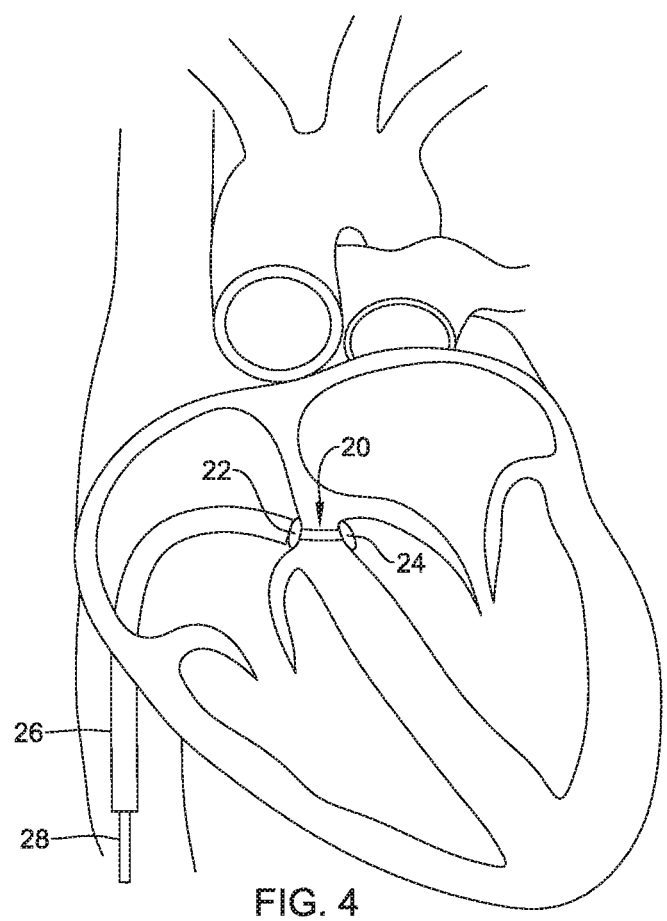
FIG. 4 is a schematic view of a human heart, showing the dual chamber LCP arrangement of FIG. 2 during deployment.

FIG. 4 provides an illustrative but non-limiting deployment example. As can be seen in FIG. 4, a delivery catheter 26 (FIG. 2) has been passed up through the IVC and into the right atrium RA. In some cases, the delivery catheter 26 may be configured to include a curved distal portion that may help direct the LCP assembly 20 into position proximate the AV septum 12. In some cases, the delivery catheter 26 may be guided into position via an interaction with a chamber wall within the right atrium RA. In some instances, the delivery catheter 26 may be a steerable catheter. While not illustrated, in some cases the delivery catheter 26 and/or the LCP assembly 20 may include radiopaque structures that are visible during imaging processes such as fluoroscopy and/or ultrasound in order to facilitate directing the delivery catheter 26 to an appropriate position proximate the AV septum 12.

Figure 5:
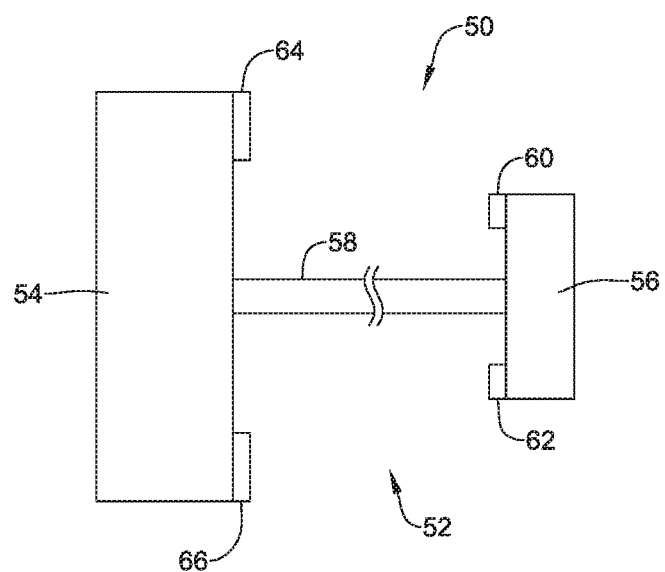
FIG. 5 is a schematic view of another implantable medical device configured for deployment across the atrioventricular septum.

FIG. 5 is a schematic view of another illustrative implantable medical device (IMD) 50 that is configured to be deployed across the AV septum 12 (FIG. 1). The illustrative IMD 50 includes a body 52 having a first end portion 54, a second end portion 56, and a connecting portion 58 that connects the first end portion 54 and the second end portion 56. In some instances, a length of the connection portion 58 may be varied in order to accommodate the cardiac anatomy of a particular patient, in order to provide better electrode contact and to optimize the electrical performance of the IMD 50. In some cases, at least part of the first end portion 54 may be configured to be positioned in the right atrium RA proximate the AV septum 12 once implanted. Likewise, at least part of the second end portion 56 may be configured to extend into the left ventricle LV once implanted. It will be appreciated that the body 52 is shown schematically in FIG. 5, including the first end portion 54 and the second end portion 56.

Once implanted, it will be appreciated that the connecting portion 58 will extend through a passage that passes across the AV septum 12. In some cases, the passage may be formed directly by the second end portion 56 being forced through the AV septum 12. In some instances, the passage may be formed by a separate needle, hypotube or other suitable device prior to inserting the second end portion 56. The second end portion 56 may extend laterally (e.g. lateral relative to the major axis of the connecting portion 58) beyond a lateral extent of the connecting portion 58 in order to engage the ventricle side 18 (FIG. 1) of the AV septum 12 once the IMD 50 is implanted. In some cases, at least part of the second end portion 56 may be configured to move from a contracted state, such as for delivery to the AV septum 12 and insertion through the AV septum 12, to an expanded state, such as for anchoring the second end portion 56 relative to the ventricle side 18 of the AV septum 12.

In some cases, as illustrated, the second end portion 56 may include electrodes for sensing and/or pacing the left ventricle LV. In some cases, the second end portion 56 may include a first electrode 60 and a second electrode 62 that are positioned on the second end portion 56 such that the first electrode 60 and the second electrode 62 are able to engage the ventricle side 18 of the AV septum 12. In some instances, the second end portion 56 may also include additional electrodes, but this is not required. In some cases, the first end portion 54 may include electrodes for sensing and/or pacing the right atrium RA. In some cases, the first end portion 54 may include a first electrode 64 and a second electrode 66 that are positioned on the first end portion 54 such that the first electrode 64 and the second electrode 66 are able to engage the atrial side 16 of the AV septum 12. In some instances, the first end portion 54 may also include additional electrodes, but this is not required.

Figure 6:
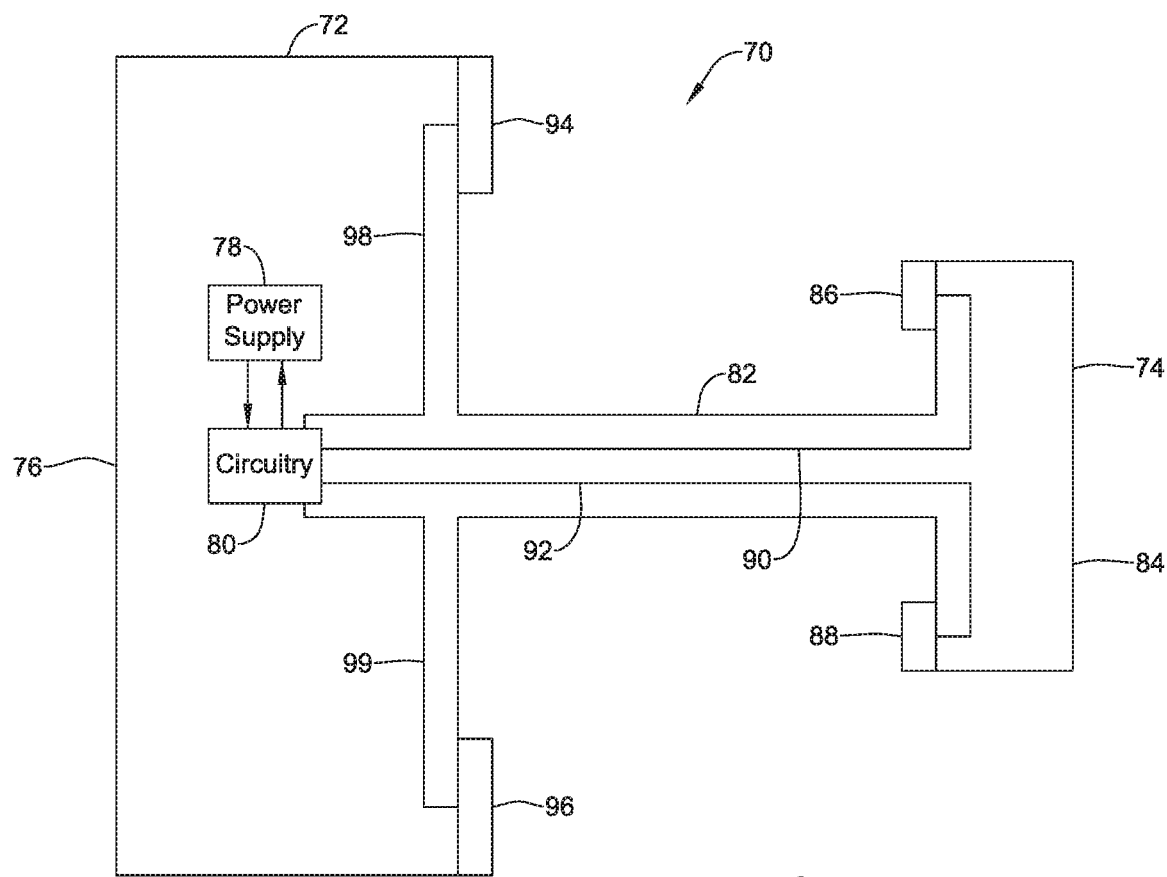
FIG. 6 is a schematic view of yet another illustrative implantable medical device configured for deployment across the atrioventricular septum.

FIG. 6 is a schematic view of another illustrative IMD 70 that is configured to be deployed across the AV septum 12 (FIG. 1) in order to sense and/or pace the heart. In some cases, as illustrated, the illustrative IMD 70 may include a first component 72 that is configured to be positioned at least in part in the right atrium RA proximate the AV septum 12 once the IMD 70 is implanted, and a second component 74 that is configured to be positioned at least in part in the left ventricle LV once the IMD 70 is implanted. In some cases, the first component 72 includes a housing 76 and a power supply 78 that is disposed within the housing 76. Circuitry 80 may be disposed within the housing 76 and may be operably coupled to the power source 78. In some cases, the power source 78 may be wirelessly rechargeable.

The second component 74 may be mechanically coupled to the first component 72 through a passage passing through the AV septum 12. In some cases, the second component 74 is mechanically coupled to the first component 72 via a connecting member 82. In some cases, the connecting member 82 may be part of the second component 74 and may form an interference fit with the first component 72. In some cases, the connecting member 82 may be part of the first component 72 and may form an interference fit with the second component 74. In some cases, the first component 72 includes a fixation element for securing the first component 72 to the AV septum 12. In some instances, the second component 74 includes a fixation element for securing the second component 74 to the AV septum 12. Subsequent drawings will provides examples of such fixation elements, which may include one or more of barbs, spikes, pins, staples, threads, screws, helix, tines, and/or the like.

In some cases, the second component 74 may include a housing 84. The housing 84 may be a cylindrical body, for example. In some cases, the housing 84 may instead have another shape, or may simply be several insulated wires coupled together and including electrodes that are electrically coupled to the insulated wires, for example. In some instances, the housing 84 could be umbrella-shaped, with electrodes disposed at the tips of wires that may be joined together in a web. A first electrode 86 and a second electrode 88 may be disposed on the housing 84 and may be positioned such that the first electrode 86 and the second electrode 88 may be able to sense and/or pace the left ventricle LV of the heart. In some cases, the first electrode 86 and the second electrode 88 are configured to engage the ventricle side 18 (FIG. 1) of the AV septum 12. In some instances, the second component 74 may also include additional electrodes, but this is not required. In some instances, the first electrode 86 and the second electrode 88 may be operably coupled to the circuitry 80 of the first component 72. In some cases, wiring leads 90 and 92 may lead from the first electrode 86 and the second electrode 88, respectively, to the circuitry 80 and may pass through or over the connecting member 82.

In some cases, the first component 72 may include electrodes for sensing and/or pacing the right atrium RA. As illustrated, the first component 72 includes a first electrode 94 and a second electrode 96. In some cases, at least one of the first electrode 94 and the second electrode 96 may be positioned to engage the atrial side 16 (FIG. 1) of the AV septum 12 once implanted. In some instances, the first component 72 may also include additional electrodes, but this is not required. In some cases, wiring leads 98 and 99 may lead from the first electrode 94 and the second electrode 96, respectively, to the circuitry 80.

In some instances, the second component 74 may be configured to move from a contracted state to an expanded state. In some cases, the second component 74 may pass through the passage formed in the AV septum 12 while in its contracted state and then move into its expanded state once the second component 74 has reached the left ventricle LV. In some cases, when in its expanded state, the second component 74 may extend laterally beyond a lateral extent of the passage through the AV septum 12 and may engage the ventricle side 18 (FIG. 1) of the AV septum 12. In some cases, the first component 72 may extend laterally beyond the lateral extent of the passage through the AV septum 12 and may engage the atrial side 16 of the AV septum 12 once the IMD 70 is implanted. In some cases, the second component 74 may be configured to cut or otherwise form the passage extending through the AV septum 12. In some instances, a separate device may be used to form the passage through the AV septum 12.

Figure 7:
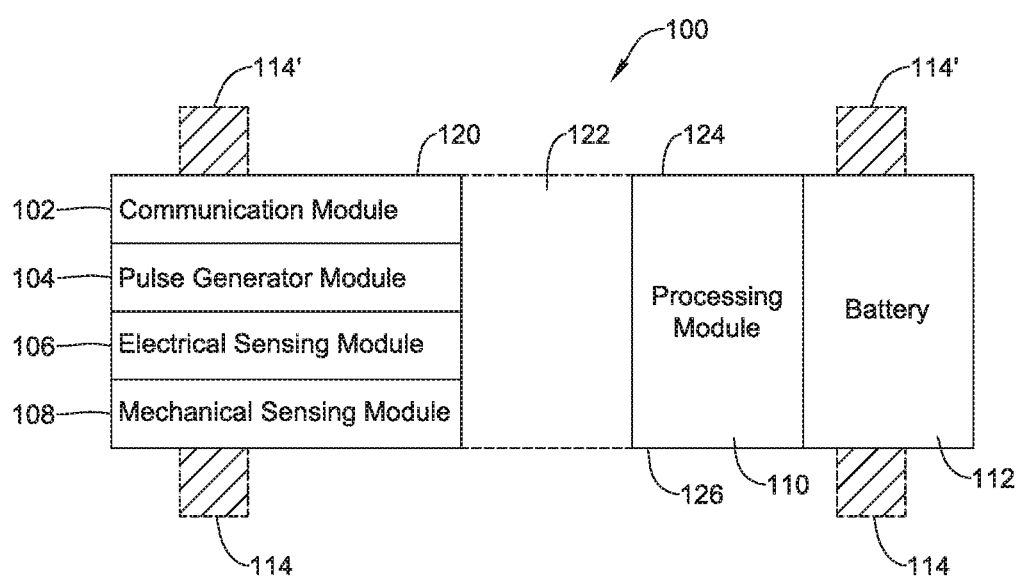
FIG. 7 is a schematic view of an illustrative LCP configured for deployment within the right atrium.

FIG. 7 is a schematic view of an illustrative LCP 100 configured for deployment within the right atrium. The LCP may be configured to sense physiological signals and parameters and deliver one or more types of electrical stimulation therapy to the atrial side 16 (FIG. 1) of the AV septum 12. Example electrical stimulation therapy may include anti-tachycardia pacing (ATP) therapy, cardiac resynchronization therapy (CRT), bradycardia therapy, various types of pacing therapy including rate responsive pacing therapy, and/or the like. The LCP 100 may be considered as an example of the right seed 22 of FIG. 2. The LCP 100 may be a compact device with all components housed within or directly on a housing 120 of the LCP 100. The illustrative LCP 100 may include a communication module 102, a pulse generator module 104, an electrical sensing module 106, a mechanical sensing module 108, a processing module 110, an energy storage module 112, and electrodes 114.

In some cases, as illustrated, the LCP 100 may include a passage 122 that passes through the LCP 100 from a first side 124 of the housing 120 to a second side 126 of the housing 120. In some cases, the passage 122 is configured to allow the left seed 24 (FIG. 2) to extend through the passage 122 during implantation of the left seed 24. In some instances, as noted with respect to FIG. 2, the passage 122 may include structure that is configured to enable electrical communication between the left seed 24 and the right seed 22. In some cases, the passage 122 may include structure to help anchor the left seed 24 to the right seed 22 after deployment. In some cases, the LCP 100 may be configured such that the first side 124 or the second side 126 of the housing 120 may be deployed along the atrial side 16 (FIG. 1) of the AV septum 12. While the passage 122 is schematically illustrated as extending through the LCP 100 at or near a midpoint of the LCP 100, it will be appreciated that in some cases the passage 122 may be located at or near one edge of the LCP 100. In some cases, the passage 122 may be defined by structure that is secured to an outer surface of the housing 120. For example, depending on the exact size and configuration of the left seed 24, the passage 122 may be formed of a cylindrical tube secured to the outside of the housing 120.

The electrodes 114 may be secured relative to the housing 120 but may be exposed to the tissue and/or blood surrounding the LCP 100. The electrodes 114 may generally conduct electrical signals to and from the LCP 100 and the surrounding tissue and/or blood. Such electrical signals can include communication pulses, electrical stimulation pulses, and intrinsic cardiac electrical signals. Intrinsic cardiac electrical signals may include electrical signals generated by the heart and may be represented by an electrocardiogram (ECG). The electrodes 114 can be made up of one or more biocompatible conductive materials such as various metals or alloys that are known to be safe for implantation within a human body. In some instances, the electrodes 114 may be generally disposed on either side of LCP 100 and may be in electrical communication with one or more of modules 102, 104, 106, 108, and 110. In examples where the electrodes 114 are secured directly to the housing 120, the electrodes 114 may have an insulative portion that electrically isolates the electrodes 114 from adjacent electrodes, the housing 120, and/or other portions of the LCP 100. Some or all of the electrodes 114 may be spaced from the housing 120 and connected to the housing 120 and/or other components of the LCP 100 through connecting wires or the like.

The electrodes 114 and/or 114' may have any of a variety of sizes and/or shapes, and may be spaced at any suitable distance. For example, the electrodes 114 may have a diameter of one to five millimeters (mm). However, in other examples, the electrodes 114 and/or 114' may have a diameter of one mm, two mm, three mm, or any other suitable diameter, dimension and shape. Example lengths for the electrodes 114 and/or 114' include a length of one mm, three mm, five mm, or any other suitable length. Additionally, at least some of the electrodes 114 and/or 114' may be spaced from one another by a distance of five mm, six mm, seven mm, or any other suitable distance. The electrodes 114 and/or 114' of a single device may have different sizes with respect to each other, and the spacing of the electrodes on the device may or may not be uniform. In some cases, the electrode 114 may be a cathode with a smaller electrode surface area and the electrode 114' may be an anode electrode with a larger electrode surface.

The communication module 102 may be electrically coupled to the electrodes 114 and/or 114' and configured to deliver communication pulses to tissues of the patient for communicating with other devices such as sensors, programmers, other medical devices, and the like. Communication pulses, as used herein, may be any modulated signal that conveys information to another device, either by itself or in conjunction with one or more other modulated signals. In some examples, communication pulses are sub-threshold signals which convey information, but this is not required. Other devices that the communication module 102 may be configured to communicate with may be located either external or internal to the patient's body. The communication module 102 may additionally be configured to sense for communication pulses delivered by the other devices, which are located externally to the LCP 100. Irrespective of the location, the LCP 100 and the other devices may communicate with each other via the communication module 102 to accomplish one or more desired functions. Some example functions include storing communicated data, using communicated data for determining occurrences of arrhythmias, coordinating delivery of electrical stimulation therapy, and/or other functions.

The LCP 100 and the other devices may use the delivered communication pulses to communicate raw information, processed information, messages, and/or other data. Raw information may include information such as sensed electrical signals (e.g. a sensed ECG), signals gathered from coupled sensors, and the like. In some examples, the raw information may include signals that have been filtered using one or more signal processing techniques. Processed information may include any information that has been determined by the LCP 100. For example, processed information may include a determined heart rate, timings of determined heartbeats, timings of other determined events, determinations of threshold crossings, expirations of monitored time periods, and determined parameters such as activity parameters, blood-oxygen parameters, blood pressure parameters, heart sound parameters, and the like. Messages may include instructions directing another device to take action, notifications of imminent actions of the sending device, requests for reading from the receiving device or writing data to the receiving device. In some cases, the LCP 100 may communicate with an S-ICD (subcutaneous implantable cardioinverter).

In at least some examples, the communication module 102 (or the LCP 100) may further include switching circuitry to selectively connect one or more of the electrodes 114 and/or 114' to the communication module 102 in order to select via which electrodes 114 and/or 114' the communication module 102 delivers the communication pulses. Additionally, the communication module 102 may be configured to use one or more methods for communicating with other devices. For example, the communication module 102 may communicate via conducted signals, radiofrequency (RF) signals, optical signals, acoustic signals, inductive coupling, and/or any other signals or methods suitable for communication with an external device such as an S-ICD or a programmer.

The pulse generator module 104 of the LCP 100 may also be electrically connected to one or more of the electrodes 114 and/or 114'. The pulse generator module 104 may be configured to generate electrical stimulation pulses and deliver the electrical stimulation pulses to tissues of a patient via the electrodes 114 and/or 114' electrodes in order to effectuate one or more electrical stimulation therapies. Electrical stimulation pulses as used herein are meant to encompass any electrical signals that may be delivered to tissue of a patient for purposes of treatment of any type of disease or abnormality. When used to treat heart diseases or abnormalities, the electrical stimulation pulses may generally be configured so as to capture the heart of the patient—cause the heart to contract in response to the delivered electrical stimulation pulse. In at least examples where the pulse generator 104 is configured to generate specific types of electrical stimulation pulses termed defibrillation/cardioversion pulses, the pulse generator module 104 may include one or more capacitor elements.

The pulse generator module 104 may include capability to modify the electrical stimulation pulses, such as by adjusting a pulse width or amplitude of the electrical stimulation pulses, in order to ensure that the delivered electrical stimulation pulses consistently capture the heart. The pulse generator module 104 may use energy stored in the energy storage module 112 to generate the electrical stimulation pulses. In at least some examples, the pulse generator module 104 (or the LCP 100) may further include switching circuitry to selectively connect one or more of the electrodes 114 and/or 114' to the pulse generator module 104 in order to select via which electrodes 114 and/or 114' the pulse generator 104 delivers the electrical stimulation pulses.

In some examples, the LCP 100 may include the electrical sensing module 106 and the mechanical sensing module 108. The electrical sensing module 106 may be configured to sense intrinsic cardiac electrical signals conducted from the electrodes 114 and/or 114' to the electrical sensing module 106. For example, the electrical sensing module 106 may be electrically connected to one or more electrodes 114 and/or 114' and the electrical sensing module 106 may be configured to receive cardiac electrical signals conducted through the electrodes 114 and/or 114'. In some examples, the cardiac electrical signals may represent local information from the chamber in which the LCP 100 is implanted. For instance, if the LCP 100 is implanted within the right atrium RA, cardiac electrical signals sensed by the LCP 100 through the electrodes 114 and/or 114' may represent atrial cardiac electrical signals. The mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. The mechanical sensing module 108 may gather signals from the sensors indicative of the various physiological parameters. Both the electrical sensing module 106 and the mechanical sensing module 108 may be further connected to the processing module 110 and may provide signals representative of the sensed cardiac electrical signals and/or physiological signals to processing the module 110. Although described with respect to FIG. 7 as separate sensing modules, in some examples, the electrical sensing module 106 and the mechanical sensing module 108 may be combined into a single module.

The processing module 110 may be configured to control the operation of the LCP 100. For example, the processing module 110 may be configured to receive cardiac electrical signals from the electrical sensing module 106 and/or physiological signals from the mechanical sensing module 108. Based on the received signals, the processing module 110 may determine occurrences and types of arrhythmias. The processing module 110 may further receive information from the communication module 102. In some examples, the processing module 110 may additionally use such received information to determine occurrences and types of arrhythmias. However, in other examples, the LCP 100 may use the received information instead of the signals received from the electrical sensing module 106 and/or the mechanical sensing module 108—for instance if the received information is more accurate than the signals received from the electrical sensing module 106 and/or the mechanical sensing module 108 or if the electrical sensing module 106 and/or the mechanical sensing module 108 have been disabled or omitted from the LCP 100.

Based on any determined arrhythmias, the processing module 110 may then control the pulse generator module 104 to generate electrical stimulation pulses in accordance with one or more electrical stimulation therapies to treat the determined arrhythmias. For example, the processing module 110 may control the pulse generator module 104 to generate pacing pulses with varying parameters and in different sequences to effectuate one or more electrical stimulation therapies. In controlling the pulse generator module 104 to deliver bradycardia pacing therapy, the processing module 110 may control the pulse generator module 104 to deliver pacing pulses designed to capture the heart of the patient at a regular interval to prevent the heart of a patient from falling below a predetermined threshold. For ATP therapy, the processing module 110 may control the pulse generator module 104 to deliver pacing pulses at a rate faster than an intrinsic heart rate of a patient in attempt to force the heart to beat in response to the delivered pacing pulses rather than in response to intrinsic cardiac electrical signals. The processing module 110 may then control the pulse generator module 104 to reduce the rate of delivered pacing pulses down to a safe level. In CRT, the processing module 110 may control the pulse generator module 104 to deliver pacing pulses in coordination with another device (e.g. the left seed 24) to cause the heart to contract more efficiently. Additionally, in cases where the pulse generator module 104 is capable of generating defibrillation and/or cardioversion pulses for defibrillation/cardioversion therapy, the processing module 110 may control the pulse generator module 104 to generate such defibrillation and/or cardioversion pulses. In some examples, the LCO 100 may instead communicate with an S-ICD for defibrillation therapy. In other examples, the processing module 110 may control the pulse generator module 104 to generate electrical stimulation pulses to provide electrical stimulation therapies different than those described herein to treat one or more detected cardiac arrhythmias.

Aside from controlling the pulse generator module 104 to generate different types of electrical stimulation pulses and in different sequences, in some examples, the processing module 110 may also control the pulse generator module 104 to generate the various electrical stimulation pulses with varying pulse parameters. For example, each electrical stimulation pulse may have a pulse width and a pulse amplitude. The processing module 110 may control the pulse generator module 104 to generate the various electrical stimulation pulses with specific pulse widths and pulse amplitudes. For example, the processing module 110 may cause the pulse generator module 104 to adjust the pulse width and/or the pulse amplitude of electrical stimulation pulses if the electrical stimulation pulses are not effectively capturing the heart. Such control of the specific parameters of the various electrical stimulation pulses may ensure that the LCP 100 is able to provide effective delivery of electrical stimulation therapy.

In some examples, the processing module 110 may further control the communication module 102 to send information to other devices. For example, the processing module 110 may control the communication module 102 to generate one or more communication pulses for communicating with other devices of a system of devices. For instance, the processing module 110 may control the communication module 102 to generate communication pulses in particular sequences, where the specific sequences convey different data to other devices. The communication module 102 may also conduct any received communication signals to the processing module 110 for potential action by the processing module 110.

In further examples, the processing module 110 may additionally control switching circuitry by which the communication module 102 and the pulse generator module 104 deliver communication pulses and electrical stimulation pulses to tissue of the patient. As described above, both the communication module 102 and the pulse generator module 104 may include circuitry for connecting one or more electrodes 114 and/114' to the communication module 102 and the pulse generator module 104 so those modules may deliver the communication pulses and electrical stimulation pulses to tissue of the patient. The specific combination of one or more electrodes by which the communication module 102 and the pulse generator module 104 deliver communication pulses and electrical stimulation pulses influence the reception of communication pulses and/or the effectiveness of electrical stimulation pulses. Although it was described that each of the communication module 102 and the pulse generator module 104 may include switching circuitry, in some examples the LCP 100 may have a single switching module connected to all of the communication module 102, the pulse generator module 104, and the electrodes 114 and/or 114'. In such examples, the processing module 110 may control the single switching module to connect the modules 102/104 and the electrodes 114/114'.

In still additional examples, the processing module 110 may control the pulse generator module 104 to generate the communication pulses for communicating with external devices. In such examples, the communication module 102 may not include the capability to generate communication pulses. In some even additional examples, the electrical sensing module 106 may further include the capability to sense communication pulses. In such examples, the electrical sensing module 106 may communicate any received communication pulses to the processing module 110. In such examples, the LCP 100 may not include the communication module 102, as the functions of the communication module 102 are subsumed within the pulse generator module 104 and the electrical sensing module 106. However, in such examples, the LCP 100 may not be able to simultaneously generate both communication pulses and electrical stimulation pulses.

In some examples, the processing module 110 may include a pre-programmed chip, such as a very-large-scale integration (VLSI) chip or an application specific integrated circuit (ASIC). In such embodiments, the chip may be pre-programmed with control logic in order to control the operation of the LCP 100. By using a pre-programmed chip, the processing module 110 may use less power than other programmable circuits while able to maintain basic functionality, thereby increasing the battery life of the LCP 100. In other examples, the processing module 110 may include a programmable microprocessor or the like. Such a programmable microprocessor may allow a user to adjust the control logic of the LCP 100 after manufacture, thereby allowing for greater flexibility of the LCP 100 than when using a pre-programmed chip.

The processing module 110, in additional examples, may further include a memory circuit and the processing module 110 may store information on and read information from the memory circuit. In other examples, the LCP 100 may include a separate memory circuit (not shown) that is in communication with the processing module 110, such that the processing module 110 may read and write information to and from the separate memory circuit. The memory circuit, whether part of the processing module 110 or separate from the processing module 110 may have address lengths of, for example, eight bits. However, in other examples, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

The energy storage module 112 may provide a power source to the LCP 100 for its operations. In some examples, the energy storage module 112 may be a non-rechargeable lithium-based battery. In other examples, the non-rechargeable battery may be made from other suitable materials known in the art. Because the LCP 100 is an implantable device, access to the LCP 100 may be limited. In such circumstances, it is necessary to have sufficient energy capacity to deliver therapy over an extended period of treatment such as days, weeks, months, or years. In some examples, the energy storage module 112 may a rechargeable battery in order to facilitate increasing the useable lifespan of the LCP 100. In still other examples, the energy storage module 112 may be other types of energy storage devices such as capacitors.

Figure 8:
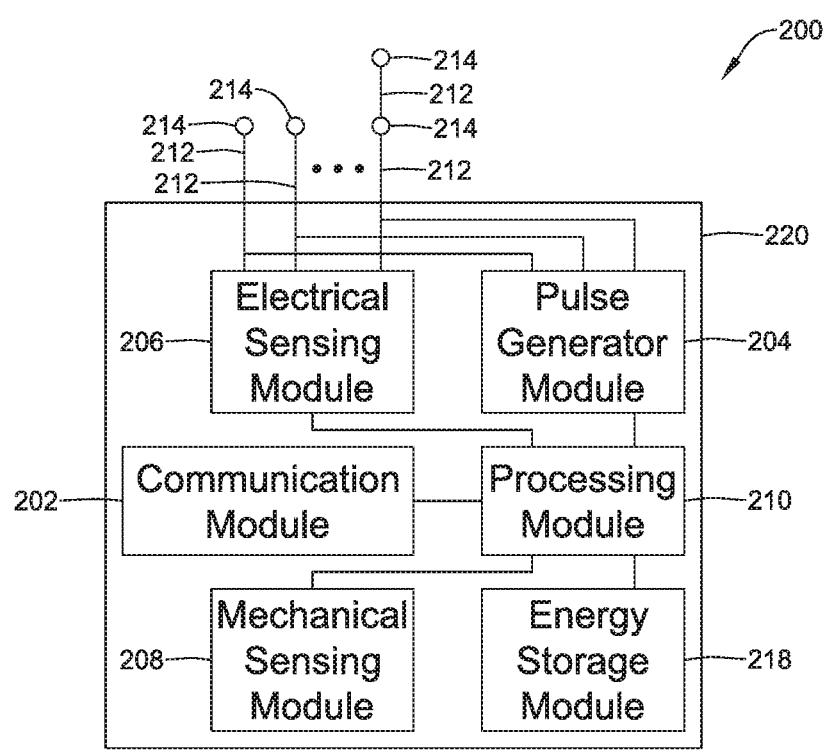
FIG. 8 is a block diagram of another illustrative LCP.

FIG. 8 is a block diagram of another illustrative LCP 200. In some cases, the LCP 200 may be considered as being an example of the right seed 22 (FIG. 2). In some cases, the LCP 200 may be considered as being an example of the left seed 24. In some instances, the components forming the LCP 200 may be split between the right seed 22 and the left seed 24.

In some cases, the LCP 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some cases, the LCP 200 may include leads such as leads 212. The leads 212 may include electrical wires that conduct electrical signals between the electrodes 214 and one or more of the modules located within housing 220. In some cases, the leads 212 may be connected to and extend away from the housing 220 of the LCP 200 in order to place electrodes 214 adjacent the atrial side 16 and/or the ventricle side 18 of the AV septum 12.

The mechanical sensing module 208, as with the mechanical sensing module 108, may contain or be electrically connected to one or more sensors, such as accelerometers, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

Figure 9:
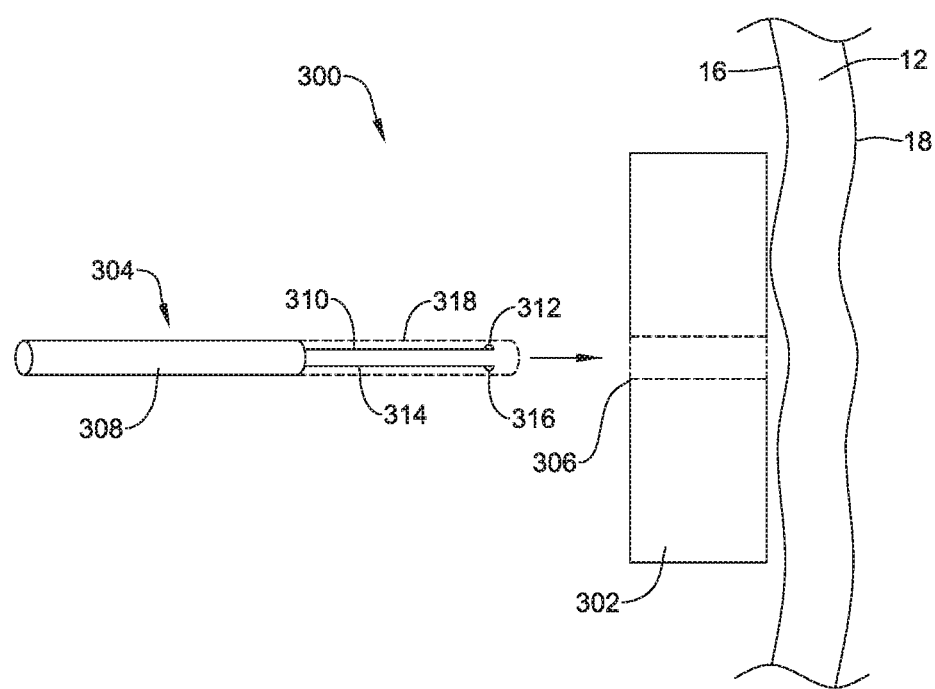
FIG. 9 is a schematic view of an illustrative two-part LCP, prior to deployment.
Figure 10:
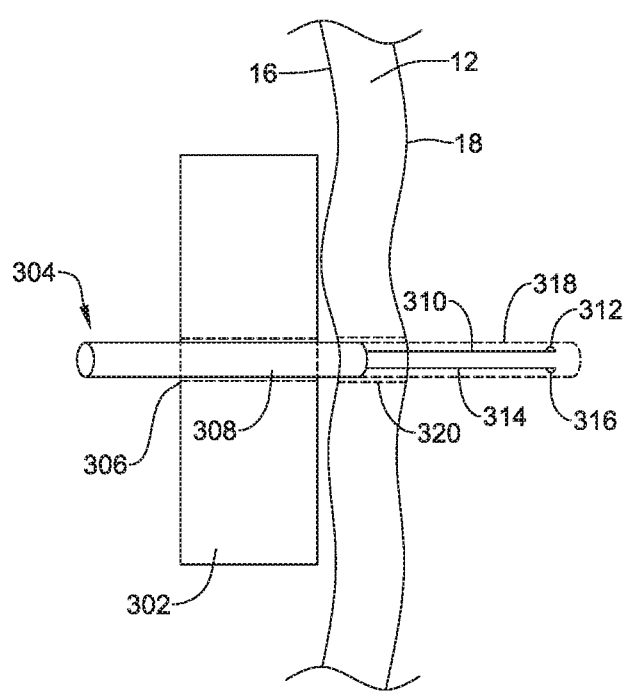
FIG. 10 is a schematic view of the illustrative two-part LCP of FIG. 9, during deployment.
Figure 11:
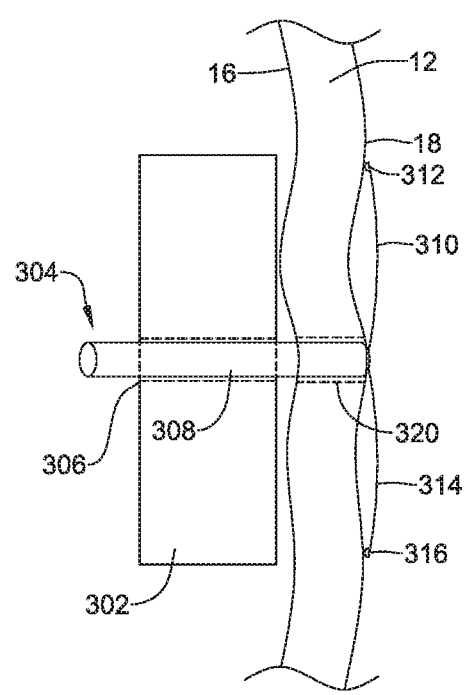
FIG. 11 is a schematic view of the illustrative two-part LCP, after deployment.

FIGS. 9 through 11 illustrate deployment of an illustrative but non-limiting example of a two-part LCP 300. The illustrative LCP assembly 300 includes a right seed 302 that is configured to remain on the atrial side 16 of the AV septum 12, and a left seed 304 that is configured to extend through a passage 306 formed within the right seed 302. As illustrated, the left seed 304 includes a cylindrical or other shaped body 308. A first electrical conduit 310 extends distally from the cylindrical body 308 and includes a first electrode 312 that is coupled to the first electrical conduit 310. A second electrical conduit 314 extends distally from the cylindrical body 308 and includes a second electrode 316 that is coupled to the second electrical conduit 314. As illustrated, the first electrical conduit 310, the first electrode 312, the second electrical conduit 314 and the second electrode 316 are captured within a distal tip 318.

The distal tip 318 holds the first and second electrical conduits 310, 314 in the illustrated position for deployment. In some cases, the distal tip 318 is dissolvable upon exposure to blood. In some cases, the distal tip 318 may be formed of a crystallized material such as sugar that is safe for dissolving in the blood stream. Accordingly, the first and second electrical conduits 310, 314 may be held in a delivery configuration for delivery and subsequently may move into a deployment configuration (as shown for example in FIG. 11) once the distal tip 318 has dissolved. In some instances, the distal tip 318 may be considered as being a sweet tip.

In FIG. 10, the left seed 304 has been advanced through the passage 306 and through a passage 320 formed within the AV septum 12. In some instances, the distal tip 318 is configured to push through the AV septum 12 to form the passage 320. In some cases, a separate device may be extended through the AV septum 12 to form the passage 320 prior to insertion of the left seed 304. In FIG. 10, the distal tip 318 is still intact. Moving to FIG. 11, it can be seen that the distal tip 318 has dissolved or otherwise disappeared, permitting the first electrical conduit 310 to move into a position in which the first electrode 312 is in contact with the ventricle side 18 of the AV septum 12 and permitting the second electrical conduit 314 to move into a position in which the second electrode 316 is in contact with the ventricle side 18 of the AV septum 12.

Figure 12:
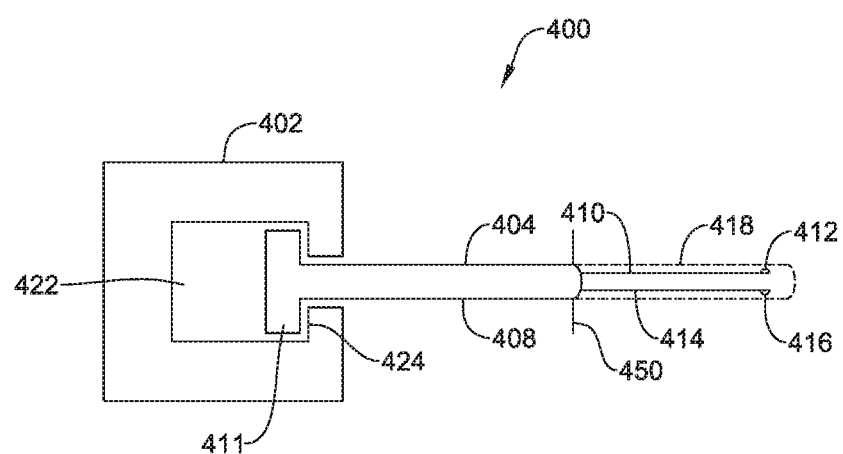
FIG. 12 is a schematic view of another illustrative two-part LCP.

FIG. 12 is a schematic view of another illustrative two-part LCP 400. The illustrative two-part LCP 400 includes a right seed 402 that is configured to remain on the atrial side 16 of the AV septum 12, and a left seed 404 that is configured to extend through a passage 406 formed within the right seed 402. As illustrated, the left seed 404 includes a cylindrical body 408. A first electrical conduit 410 extends distally from the cylindrical body 408 and includes a first electrode 412 that is coupled to the first electrical conduit 410. A second electrical conduit 414 extends distally from the cylindrical body 408 and includes a second electrode 416 that is coupled to the second electrical conduit 414. As illustrated, the first electrical conduit 410, the first electrode 412, the second electrical conduit 414 and the second electrode 416 are captured within a distal tip 418 that in some cases may be a sweet tip as discussed with respect to FIGS. 9 through 11. Once deployed, the distal tip 418 may dissolve or otherwise disappear, and the first electrical conduit 410 and the second electrical conduit 414 may be able to move into a deployed configuration in which the first electrode 412 and the second electrode 416 are positioned against the ventricle side 18 of the AV septum 12.

The cylindrical body 408 may include a proximal end 411 that is slidingly disposed within a chamber 422 that is formed within the right seed 402. It will be appreciated that the chamber 422 includes a distal end 424 that is configured to limit axial travel of the proximal end 411 of the left seed 404. Accordingly, the interaction between the proximal end 411 of the left seed 404 and the distal end 424 of the chamber 422 of the right seed 402 limits how far the left seed 404 can extend into the left ventricle LV. Once the distal tip 418 has dissolved or otherwise disappeared, the first and second electrical conduits 410 and 414 move into position against the ventricle side 18 of the AV septum 12, thereby limiting movement of the left seed 404 back towards the right atrium RA. Thus, the left seed 404 is locked in position relative to the right seed 402 and relative to the AV septum 12. In some embodiments, the left seed 404 may include a membrane 450 that may help to secure between the left seed 404 and the ventricle side 18 of the AV septum 12. In some cases, the membrane 450 may be formed of a flexible material such as silicone, and may be impregnated with a salt or other material that will cause the membrane 450 to swell upon exposure to blood. In some instances, the membrane 450 may have a folded down configuration for deployment of the left seed 404 and may subsequently revert to the expanded configuration shown in FIG. 12.

Figure 13:
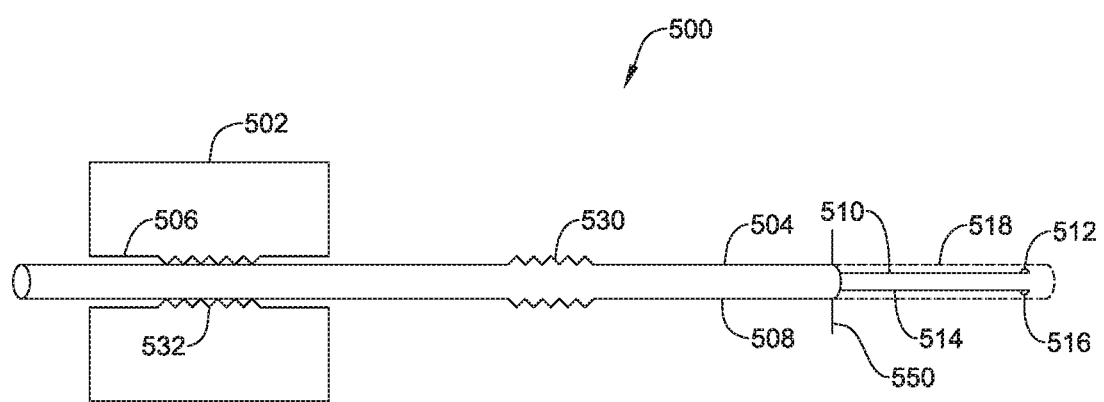
FIG. 13 is a schematic view of yet another illustrative two-part LCP.

FIG. 13 is a schematic view of yet another illustrative two-part LCP 500. The illustrative LCP 500 includes a right seed 502 that is configured to remain on the atrial side 16 of the AV septum 12 and a left seed 504 that is configured to extend through a passage 506 formed within the right seed 502. As illustrated, the left seed 504 includes a cylindrical body 508. A first electrical conduit 510 extends distally from the cylindrical body 508 and includes a first electrode 512 that is coupled to the first electrical conduit 510. A second electrical conduit 514 extends distally from the cylindrical body 508 and includes a second electrode 516 that is coupled to the second electrical conduit 514. As illustrated, the first electrical conduit 510, the first electrode 512, the second electrical conduit 514 and the second electrode 516 are captured within a distal tip 518 that in some cases may be a sweet tip as discussed with respect to FIGS. 9 through 11.

In the example shown, the cylindrical body 508 of the left seed 504 includes a ratchet section 530 that is configured to interact with a corresponding ratchet section 532 disposed within the passage 506 formed within the right seed 502. In order to implant the LCP 500, the LCP 500 may be delivered to the right atrium RA with the left seed 504 disposed within the right seed 502 as illustrated, i.e., with the ratchet section 530 positioned outside of the right seed 502. Alternatively, the left seed 504 may be delivered to the right atrium RA and then the right seed 502 may be advanced over the left seed 504.

Once the left seed 504 has been advanced through the AV septum 12, and the distal tip 518 has dissolved or otherwise disappeared, the electrical conduits 510 and 514 may move the electrodes 512 and 516, respectively, into position against the ventricle side 18 of the AV septum 12. The left seed 504 may then be pulled back through the right seed 502 such that the ratchet section 530 engages the ratchet section 532. The ratchet sections 530 and 532 may be configured to permit the ratchet section 530 to move right to left (in the illustrated orientation), relative to the ratchet section 532 but not permit the ratchet section 530 to move left to right relative to the ratchet section 532. It will be appreciated that FIG. 13 is not to scale, and that the relative dimensions may vary in order to accommodate a particular patient's cardiac architecture.

In some embodiments, the left seed 504 may include a membrane 550 that may help to secure between the left seed 504 and the ventricle side 18 of the AV septum 12 and prevent blood from moving towards the right atrium RA after removal of a deployment device. In some cases, the membrane 550 may be formed of a flexible material such as silicone, and may be impregnated with a salt or other material that will cause the membrane 550 to swell upon exposure to blood. In some instances, the membrane 550 may have a folded down configuration for deployment of the left seed 504 and may subsequently revert to the expanded configuration shown in FIG. 13.

Figure 14:
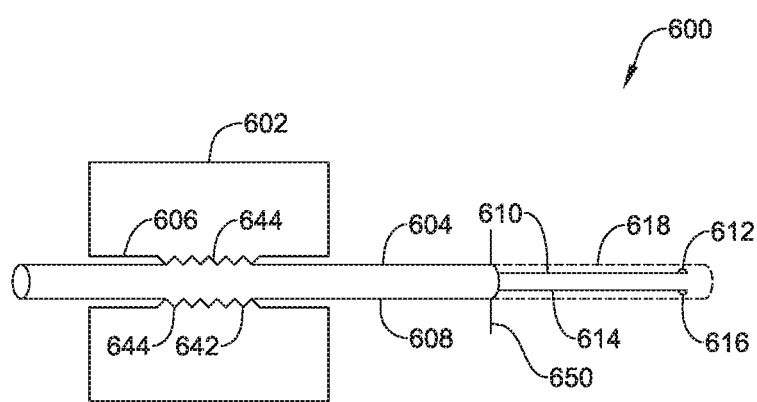
FIG. 14 is a schematic view of another illustrative two-part LCP.

FIG. 14 is a schematic view of another illustrative two-part LCP 600. The illustrative LCP 600 includes a right seed 602 that is configured to remain on the atrial side 16 of the AV septum 12, and a left seed 604 that is configured to extend through a passage 606 formed within the right seed 602. As illustrated, the left seed 604 includes a cylindrical body 608. A first electrical conduit 610 extends distally from the cylindrical body 608 and includes a first electrode 612 that is coupled to the first electrical conduit 610. A second electrical conduit 614 extends distally from the cylindrical body 608 and includes a second electrode 616 that is coupled to the second electrical conduit 614. As illustrated, the first electrical conduit 610, the first electrode 612, the second electrical conduit 614 and the second electrode 616 are captured within a distal tip 618 that in some cases may be a sweet tip.

In some cases, the cylindrical body 608 of the left seed 604 may include a threaded portion 640 that threadedly engages a corresponding threaded portion 642 formed within the passage 606. Accordingly, advancement of the left seed 604 relative to the right seed 602 may be closely controlled. Once the left seed 604 has been deployed, the distal tip 618 may dissolve or otherwise disappear, and the first electrical conduit 610 and the second electrical conduit 614 may be able to move into a deployed configuration in which the first electrode 612 and the second electrode 616 are positioned against the ventricle side 18 of the AV septum 12. The left seed 604 may then be moved backward relative to the right seed 602 in order to lock the left seed 604 in place relative to the AV septum 12 and relative to the right seed 602 by rotating the left seed 604 in an opposite direction to that used to advance the left seed 604. In some cases, the threaded portion 642 may include a vinyl bump or other structure 644 that serves to lock the left seed 604 in position and not permit undesired movement after implantation.

In some embodiments, the left seed 604 may include a membrane 650 that may help to secure between the left seed 504 and the ventricle side 18 of the AV septum 12. In some cases, the membrane 550 may be formed of a flexible material such as silicone, and may be impregnated with a salt or other material that will cause the membrane 650 to swell upon exposure to blood. In some instances, the membrane 650 may have a folded down configuration for deployment of the left seed 604 and may subsequently revert to the expanded configuration shown in FIG. 14.

Figure 15:
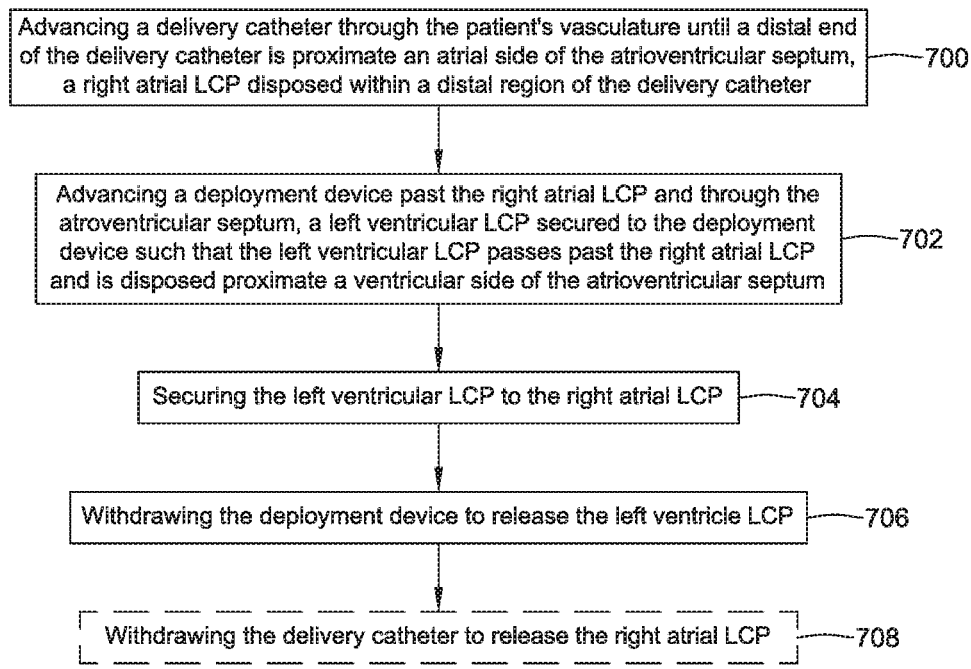
FIG. 15 is a flow diagram showing an illustrative implantation method.

FIG. 15 is a flow diagram showing an illustrative method of deploying a leadless pacing and sensing assembly proximate a patient's atrioventricular septum. The leadless pacing and sensing assembly may include a right atrial leadless cardiac pacemaker (LCP) and a left ventricular leadless cardiac pacemaker (LCP). A delivery catheter may be advanced through the patient's vasculature until a distal end of the delivery catheter is proximate an atrial side of the atrioventricular septum. The right atrial LCP may be disposed within a distal region of the delivery catheter as generally indicated at block 700. A deployment device may be advanced past the right atrial LCP and through the atrioventricular septum. The left ventricular LCP, sometimes secured to the deployment device, may be passed past the right atrial LCP and disposed in the left ventricle and proximate a ventricular side of the atrioventricular septum as generally seen at block 702. In some cases, the relative spacing and/or positioning of the right atrial LCP and the left ventricular LCP may be adjusted to improve pacing and/or sensing performance of the right atrial LCP and/or the left ventricular LCP by, for example, improving contact between one or more electrodes and the atrioventricular septum. The right atrial LCP and/or the left ventricular LCP may, for example, be activated to test performance before their final positions are secured. As indicated at block 704, the left ventricular LCP may be secured to the right atrial LCP. In some instances, the left ventricular LCP may then be released from the deployment device. The deployment device may be withdrawn as seen at block 706. The delivery catheter may be withdrawn as indicated at block 708. In some cases, withdrawing the delivery catheter may release the right atrial LCP.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. An implantable medical device (IMD) configured for deployment at a patient's atrioventricular septum in order to sense and/or pace a patient's heart, the atrioventricular septum of the patient's heart having an atrial facing side defining part of the right atrium of the patient's heart and a ventricle facing side defining part of the left ventricle of the patient's heart, the IMD comprising:
    a first component configured to be positioned at least in part in the right atrium of the patient's heart proximate the atrioventricular septum once the IMD is implanted, the first component comprising:
        a housing;
        a power source disposed within the housing; and
        circuitry disposed within the housing and operably coupled to the power source;
        one or more electrodes operatively coupled to the circuitry for pacing the atrial facing side of the patient's heart; and
        a passageway defined by the housing;

a second component configured to be positioned at least in part in the left ventricle of the patient's heart once the IMD is implanted, wherein the first component and the second component are configured such that the second component is translatable in its entirety relative to the first component, the second component is translatable through at least part of the passageway defined by the housing of the first component during deployment of the IMD and is configured to extend through the patient's atrioventricular septum and into the left ventricle of the patient's heart, the second component comprising:
  a housing;
  two or more electrodes for sensing and/or pacing the left ventricle of the patient's heart.

2. The IMD of claim 1, wherein the two or more electrodes of the second component are operably coupled to the circuitry of the first component.

3. The IMD of claim 1, wherein at least one of the two or more electrodes of the second component are configured to engage the ventricle facing side of the atrioventricular septum of the patient's heart once the IMD is implanted laterally where the second component is configured to extend through the patient's atrioventricular septum and into the left ventricle of the patient's heart.

4. The IMD of claim 1, wherein at least one of the two or more electrodes of the first component is configured to engage the atrial facing side of the atrioventricular septum of the patient's heart once the IMD is implanted.

5. The IMD of claim 1, wherein at least part of the second component is configured to move from a contracted state to an expanded state, wherein during implantation of the IMD, the second component is configured to pass through the atrioventricular septum in the contracted state and then move to the expanded state once in the left ventricle of the patient's heart.

6. The IMD of claim 5, wherein in the expanded state, the second component is configured to extend laterally beyond a lateral extent of where the second component would extend through the patient's atrioventricular septum and into the left ventricle of the patient's heart before engaging the left ventricle facing side of the atrioventricular septum of the patient's heart.

7. The IMD of claim 1, wherein the first component is configured to extend laterally beyond the lateral extent of the passageway defined by the housing with one or more of the electrodes of the first component configured to engage the atrial facing side of the atrioventricular septum of the patient's heart once the IMD is implanted.

8. The IMD of claim 1, wherein the second component is configured to cut a passage through the atrioventricular septum while the IMD is implanted.

9. The IMD of claim 1, wherein the second component is mechanically coupled to the first component through the passageway via a connecting member.

10. The IMD of claim 9, wherein the connecting member is part of the second component, and forms an interference fit with the first component.

11. The IMD of claim 9, wherein the connecting member is part of the first component, and forms an interference fit with the first component.

12. The IMD of claim 1, wherein the first component comprises a fixation element configured to secure the first component to the atrioventricular septum of the patient's heart.

13. The IMD of claim 1, wherein the second component comprises a fixation element configured to secure the second component to the atrioventricular septum of the patient's heart.

14. An implantable medical device (IMD) configured for deployment at a patient's atrioventricular septum, the atrioventricular septum of the patient's heart having an atrial facing side defining part of the right atrium of the patient's heart and a ventricle facing side defining part of the left ventricle of the patient's heart, the IMD comprising:
  a right seed that is configured to remain on the atrial facing side of the right atrium of the patient's heart for pacing the atrial facing side of the patient's heart, the right seed comprising:
    a right seed housing;
    a battery disposed within the right seed housing;
    control electronics disposed within the right seed housing;
    one or more electrodes operatively coupled to the control electronics for pacing the atrial facing side of the patient's heart; and
    a passageway defined by the right seed housing;
  a left seed that is configured to translate in its entirety relative to the right seed, the left seed translating through at least part of the passageway defined by the right seed housing during deployment of the IMD, through the patient's atrioventricular septum, and into the left ventricle of the patient's heart, the left seed comprising:
    a body having a first end portion, a second end portion and a connecting portion connecting the first end portion to the second end portion;
    at least part of the first end portion configured to be connected to the right seed once the IMD is implanted;
    at least part of the second end portion of the body of the left seed configured to extend into the left ventricle of the patient's heart once the IMD is implanted;
    the connecting portion configured to extend through a passage that passes through the atrioventricular septum; and
    the second end portion of the body of the left seed including one or more electrodes for sensing and/or pacing the left ventricle of the patient's heart, the second end portion extending laterally beyond a lateral extent of the connecting portion such that at least one of the one or more electrodes of the second end portion is configured to engage the ventricle facing side of the atrioventricular septum of the patient's heart laterally beyond the lateral extent of the connecting portion once the IMD is implanted.

15. The IMD of claim 14, wherein the one or more electrodes of the second end portion of the left seed are operatively connected to the control electronics of the right seed through the connecting portion of the left seed.

16. The IMD of claim 14, wherein at least part of the second end portion is configured to move from a contracted state to an expanded state during deployment of the IMD.

17. A method of deploying a leadless pacing and sensing assembly proximate a patient's atrioventricular septum, the leadless pacing and sensing assembly including a right atrial leadless cardiac pacemaker (LCP) and a left ventricular leadless cardiac pacemaker (LCP), the method comprising:
  advancing a delivery catheter through the patient's vasculature until a distal end of the delivery catheter is proximate an atrial side of the atrioventricular septum, the right atrial LCP disposed within a distal region of the delivery catheter;

advancing a deployment device through a passageway extending through the right atrial LCP and through the atrioventricular septum, the left ventricular LCP secured to the deployment device such that the left ventricular LCP extends through the right atrial LCP and is disposed proximate a ventricular side of the atrioventricular septum, the left ventricular LCP including one or more electrodes configured to extend laterally past a lateral extent of the passageway and to engage the ventricle facing side of the atrioventricular septum of the patient's heart;

securing the left ventricular LCP to the right atrial LCP; and withdrawing the deployment device.

18. The method of claim 17, further comprising withdrawing the delivery catheter.

* * * * *